United States Patent
Schmoker et al.

(10) Patent No.: US 7,066,921 B2
(45) Date of Patent: Jun. 27, 2006

(54) DISPOSABLE UNDERGARMENT WITH BODY CONFORMING FIT AND CONTAINMENT POCKET

(75) Inventors: Suzanne M. Schmoker, Oshkosh, WI (US); Cindy Lou Price, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 121 days.

(21) Appl. No.: 10/744,587

(22) Filed: Dec. 22, 2003

(65) Prior Publication Data

US 2005/0137550 A1    Jun. 23, 2005

(51) Int. Cl.
*A61F 13/15* (2006.01)

(52) U.S. Cl. .................... 604/385.01; 604/385.19; 604/385.24

(58) Field of Classification Search ........... 604/385.01, 604/385.19, 385.22, 385.23, 385.24, 392–402
See application file for complete search history.

(56) References Cited

U.S. PATENT DOCUMENTS

| | | | |
|---|---|---|---|
| 4,402,688 A | 9/1983 | Julemont | |
| 4,753,646 A | 6/1988 | Enloe | |
| 4,938,755 A | 7/1990 | Foreman | |
| 5,360,422 A | 11/1994 | Brownlee et al. | |
| 5,368,584 A | 11/1994 | Clear et al. | |
| 5,397,318 A | 3/1995 | Dreier | |
| 5,454,803 A | 10/1995 | Sageser et al. | |
| 5,527,302 A | 6/1996 | Endres et al. | |
| 5,649,918 A | 7/1997 | Schleinz | |
| 5,772,649 A * | 6/1998 | Siudzinski | 604/386 |
| 5,897,544 A * | 4/1999 | Ronnberg | 604/385.19 |
| 5,938,652 A | 8/1999 | Sauer | |
| 6,132,409 A | 10/2000 | Vogt et al. | |
| 6,132,410 A | 10/2000 | Van Gompel et al. | |
| 6,217,563 B1 | 4/2001 | Van Gompel et al. | |
| 6,264,639 B1 | 7/2001 | Sauer | |
| 6,264,641 B1 | 7/2001 | Van Gompel et al. | |
| 6,312,420 B1 | 11/2001 | Sasaki et al. | |
| 6,336,922 B1 | 1/2002 | Van Gompel et al. | |
| 6,361,527 B1 | 3/2002 | Van Gompel et al. | |
| 6,454,750 B1 | 9/2002 | Vogt et al. | |
| 6,506,185 B1 | 1/2003 | Sauer et al. | |
| 6,514,233 B1 | 2/2003 | Glaug | |
| 6,514,235 B1 | 2/2003 | Freiburger et al. | |
| 6,755,808 B1 * | 6/2004 | Balogh et al. | 604/385.28 |
| 2004/0243089 A1 * | 12/2004 | Veith et al. | 604/385.22 |

(Continued)

FOREIGN PATENT DOCUMENTS

EP    0976373    7/1998

(Continued)

*Primary Examiner*—Tatyana Zalukaeva
*Assistant Examiner*—Michael G. Bogart
(74) *Attorney, Agent, or Firm*—Brinks Hofer Gilson & Lione

(57) ABSTRACT

A disposable undergarment includes a front body panel having a body side and a garment side, a rear body panel having a body side and a garment side, and an absorbent composite connected to the front body panel and having a front terminal edge and a rear terminal edge. The rear terminal edge of the absorbent composite is connected to the garment side of the rear body panel. The front terminal edge of the absorbent composite may be connected to the body side of the front body panel. The front body panel and/or the rear body panel may be stretchable and may include an elastic material. A method of using the disposable undergarment includes stretching at least one of the front body panel and the rear body panel.

25 Claims, 4 Drawing Sheets

U.S. PATENT DOCUMENTS

| | | | |
|---|---|---|---|
| 2005/0020992 A1* | 1/2005 | Van Gompel et al. | 604/385.01 |
| 2005/0107761 A1* | 5/2005 | Mishima et al. | 604/385.25 |
| 2005/0131365 A1* | 6/2005 | Sakaguchi | 604/367 |

FOREIGN PATENT DOCUMENTS

| | | |
|---|---|---|
| EP | 1089692 | 6/1999 |
| EP | 0 796 066 B1 | 2/2000 |
| EP | 1 224 922 A2 | 7/2002 |
| WO | WO 99/56688 | 11/1999 |
| WO | WO 99/63921 | 12/1999 |
| WO | WO 00/30584 | 6/2000 |
| WO | WO 00/47152 | 8/2000 |
| WO | WO 01/28481 A1 | 4/2001 |
| WO | WO 03/039423 A1 | 5/2003 |

* cited by examiner

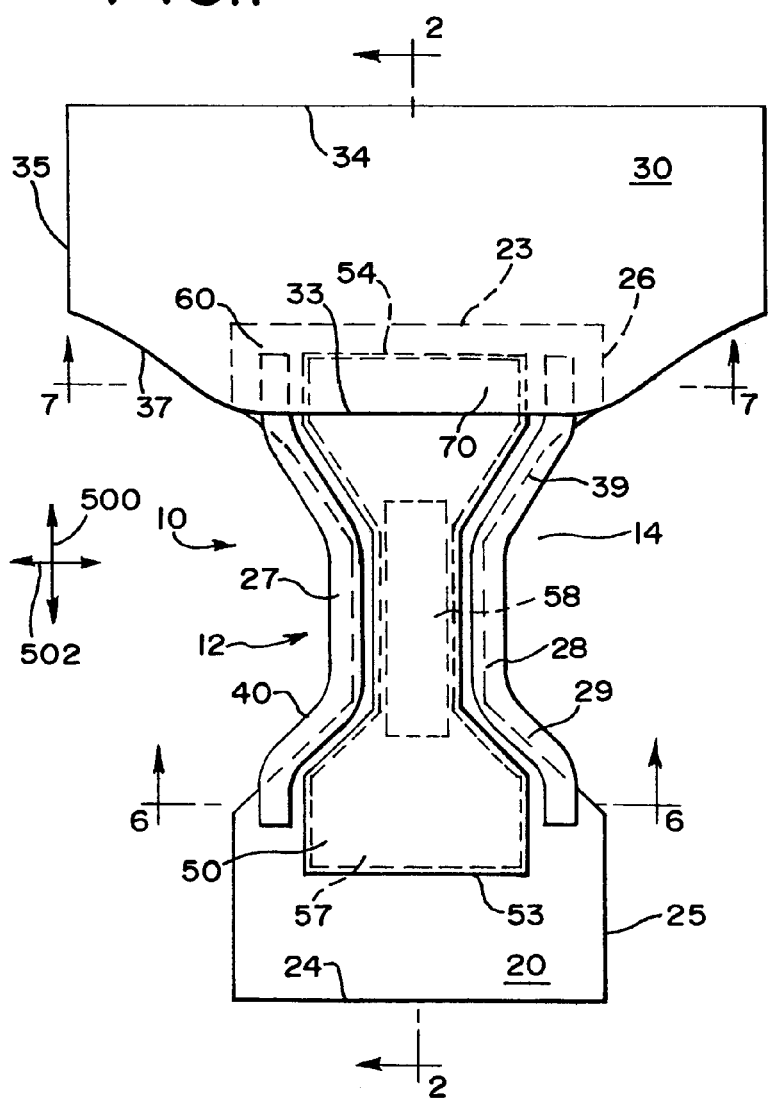
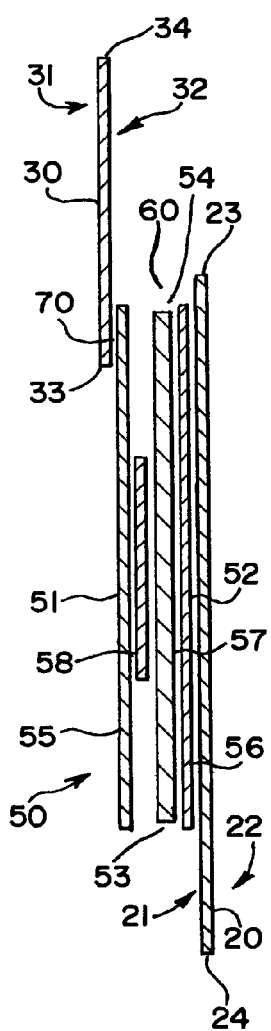

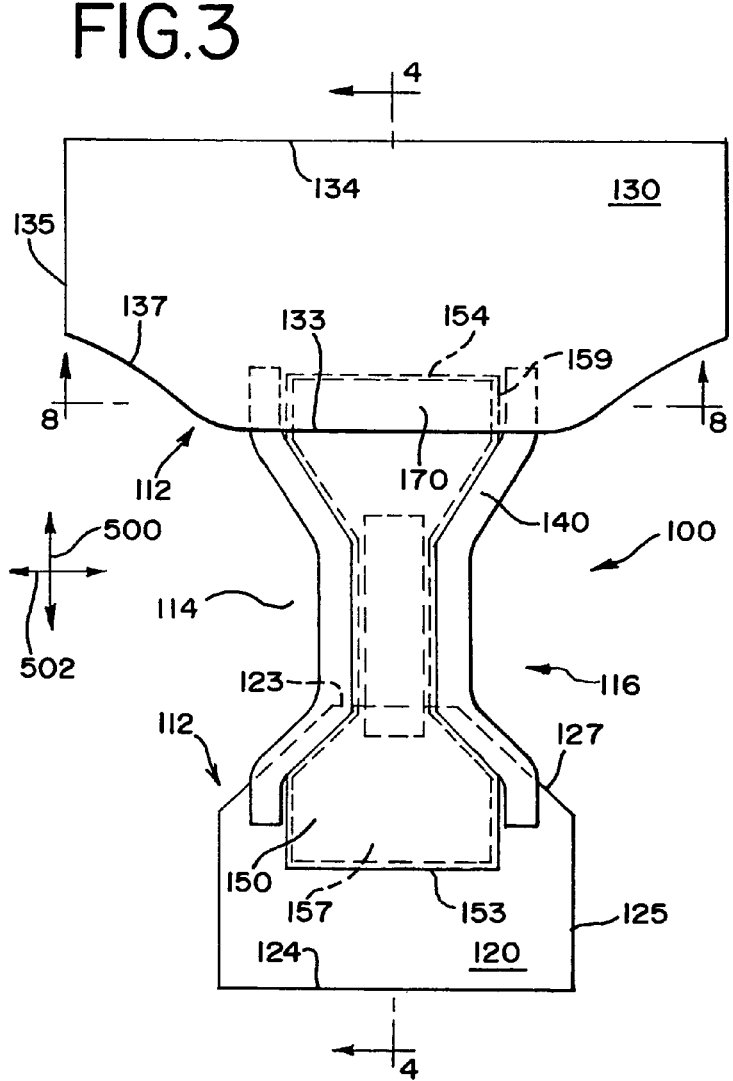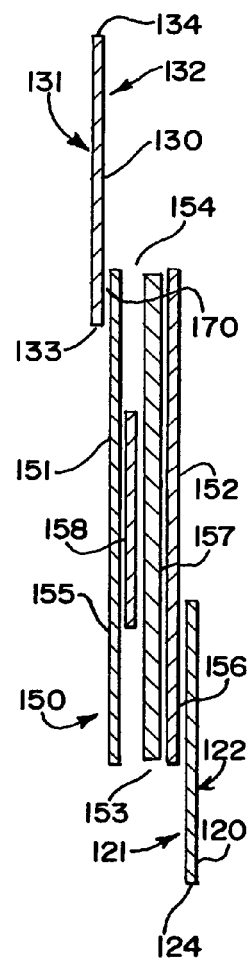

DISPOSABLE UNDERGARMENT WITH BODY CONFORMING FIT AND CONTAINMENT POCKET

BACKGROUND

The present invention relates generally to disposable undergarments, and in particular, to an undergarment having an absorbent composite, and to the method for the use thereof.

Disposable undergarments can be configured in many different forms. For example, disposable absorbent garments can be configured as a pant-type, pull-on garment, or as a diaper-type product that is drawn up between the legs and fastened about the waist with various fastening systems. In some configurations, the garment is formed from an absorbent composite attached to a front and back portions of a body chassis. Often, the body chassis and/or the absorbent composite can be overly bulky, resulting in unsightly bulges and discontinuities in the surface of the clothing that is worn over the undergarment. Over time, the bulkiness can also lead to a reduced fit of the undergarment to the body of the user.

Therefore the need remains for an improved undergarment that conforms to the body of the user during use without interference from bulky materials.

SUMMARY

In an embodiment of the invention, there is provided a disposable undergarment, comprising a front body panel comprising a body side and a garment side, a rear body panel comprising a body side and a garment side, and an absorbent composite connected to the front body panel and comprising a front terminal edge and a rear terminal edge. The rear terminal edge of the absorbent composite is connected to the garment side of the rear body panel.

These embodiments may further include a disposable undergarment wherein the rear body panel is stretchable and comprises an elastic material; wherein the front body panel is extensible; wherein the front body panel is stretchable and comprises an elastic material and the rear body panel is extensible; and wherein the absorbent composite is connected to the body side of the front body panel.

These embodiments may further include a disposable undergarment wherein the front body panel comprises a terminal waist edge and a terminal rear edge, the rear body panel comprises a terminal waist edge and a terminal front edge, and the absorbent composite is connected to the body side of the front body panel. The terminal rear edge of the front body panel overlaps the terminal front edge of the rear body panel, such that the body side of the front body panel is connected to the garment side of the rear body panel. A portion of the terminal front edge of the rear body panel may not be connected to the front body panel; the rear terminal edge of the absorbent composite may overlap the terminal front edge of the rear body panel; and at least a portion of the terminal front edge of the rear body panel may not be connected to the absorbent composite.

These embodiments may further include a disposable undergarment wherein the front body panel comprises a terminal waist edge and a terminal rear edge, the rear body panel comprises a terminal waist edge and a terminal front edge, and the terminal rear edge of the front body panel is longitudinally spaced from and forms a gap with the terminal front edge of the rear body panel. The absorbent composite bridges the gap between the front and rear body panels, and the rear terminal edge of the absorbent composite overlaps the terminal front edge of the rear body panel. The front terminal edge of the absorbent composite may overlap the terminal rear edge of the front body panel; the absorbent composite may be connected to the body side of the front body panel; and at least a portion of the terminal front edge of the rear body panel may not be connected to the absorbent composite.

In another embodiment of the invention, there is provided a disposable undergarment, comprising a front body panel comprising a body side, a garment side, a terminal waist edge and a terminal rear edge; a rear body panel comprising a body side, a garment side, a terminal waist edge and a terminal front edge; and an absorbent composite connected to the front body panel, the absorbent composite comprising a front terminal edge and a rear terminal edge. The rear body panel is stretchable and comprises an elastic material; the terminal rear edge of the front body panel overlaps the terminal front edge of the rear body panel, such that the body side of the front body panel is connected to the garment side of the rear body panel; and the rear terminal edge of the absorbent composite overlaps the terminal front edge of the rear body panel to form an overlap region.

These embodiments may further include a disposable undergarment wherein the elastic material comprises an elastic film; wherein the front body panel is extensible; wherein the rear body panel further comprises a barrier flap extending from the terminal front edge into the overlap region; and wherein the overlap region comprises additional absorbent material.

In another embodiment of the invention, there is provided a disposable undergarment, comprising a front body panel comprising a body side, a garment side, a terminal waist edge and a terminal rear edge; a rear body panel comprising a body side, a garment side, a terminal waist edge and a terminal front edge; wherein the terminal rear edge of the front body panel is longitudinally spaced from and forms a gap with the terminal front edge of the rear body panel; and an absorbent composite bridging the gap and comprising a front terminal edge and a rear terminal edge. The rear body panel is stretchable and comprises an elastic material; the rear terminal edge of the absorbent composite overlaps the terminal front edge of the rear body panel and is connected to the garment side of the rear body panel to form an overlap region; and the front terminal edge of the absorbent composite overlaps the terminal rear edge of the front body panel and is connected to the front body panel.

These embodiments may further include a disposable undergarment wherein the elastic material comprises an elastic film; wherein the front body panel is extensible; wherein the rear body panel further comprises a barrier flap extending from the terminal front edge into the overlap region; and wherein the overlap region comprises additional absorbent material.

In another embodiment of the invention, there is provided a method of using a disposable undergarment, comprising providing a front body panel, a rear body panel and an absorbent composite connected to the front body panel; and stretching at least one of the front body panel and the rear body panel. The front and rear body panels each comprise a body side and a garment side; and the absorbent composite comprises a front terminal edge and a rear terminal edge, wherein the rear terminal edge of the absorbent composite is connected to the garment side of the rear body panel.

In another embodiment of the invention, there is provided a method of instructing a user in the use of a disposable undergarment, comprising providing a front body panel, a rear body panel and an absorbent composite connected to the front body panel; instructing the user to apply the undergarment to a body; and advising the user that the application of the undergarment to the body will stretch at least one of the front body panel and the rear body panel in at least one direction. The front and rear body panels each comprise a body side and a garment side; and the absorbent composite comprises a front terminal edge and a rear terminal edge, wherein the rear terminal edge of the absorbent composite is connected to the garment side of the rear body panel.

BRIEF DESCRIPTION OF THE DRAWINGS

Many of the features and dimensions portrayed in the drawings, and in particular the presentation of layer thicknesses and the like, and the spacing therebetween, have been somewhat exaggerated for the sake of illustration and clarity.

FIG. 1 is a plan view of one example of a disposable undergarment taken from the body side thereof.

FIG. 2 is a schematic illustration of a cross-sectional view of the disposable undergarment taken along line 2—2 in FIG. 1.

FIG. 3 is a plan view of another example of a disposable undergarment taken from the body side thereof.

FIG. 4 is a schematic illustration of a cross-sectional view of the disposable undergarment taken along line 4—4 in FIG. 3.

DETAILED DESCRIPTION

Figure 5:
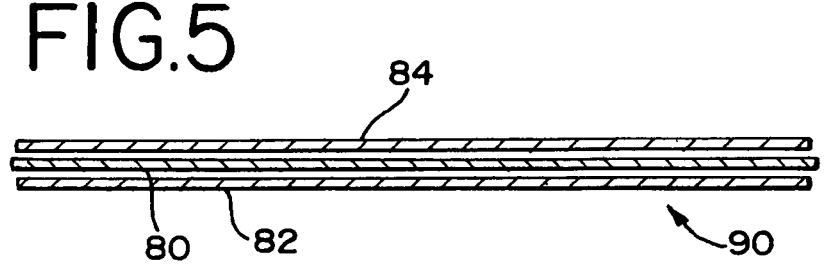
FIG. 5 is a schematic illustration of a cross-sectional view of a rear body panel.
Figure 6:
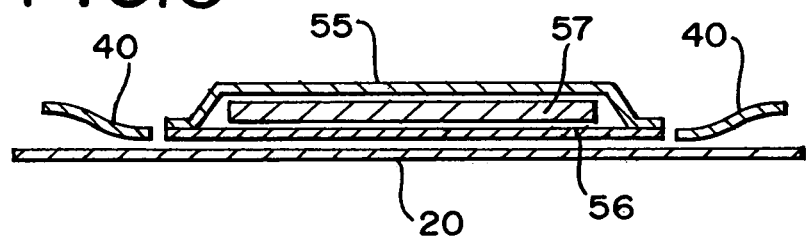
FIG. 6 is a schematic illustration of a cross-sectional view of the disposable undergarment taken along line 6—6 in FIG. 1.
Figure 7:
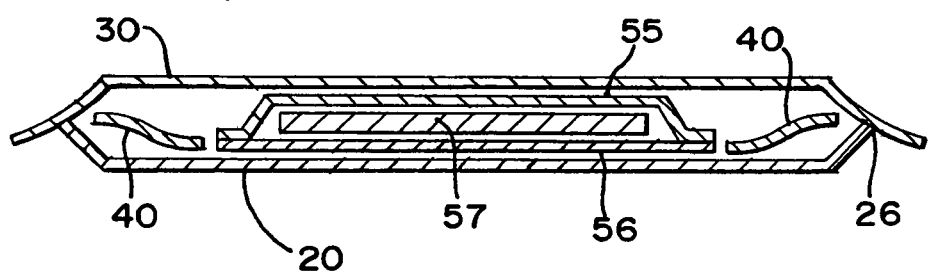
FIG. 7 is a schematic illustration of a cross-sectional view of the disposable undergarment taken along line 7—7 in FIG. 1.

The following detailed description is made in the context of a disposable diaper which is adapted to be worn by a user about the lower torso. It is readily apparent, however, that the present invention is also applicable with other absorbent articles, such as incontinence garments, training pants, and other similar articles, which are used by an infant, a child or an adult to absorb or contain bodily exudates.

It should be understood that the term "longitudinal," as used herein, means of or relating to length or the lengthwise direction 500. The term "laterally," as used herein, means situated on, directed toward or running from side to side. The term "first direction" generally refers to a path, line or course rather than a vector, and includes and applies equally to opposite orientations along the path, line or course, including for example and without limitation movement along a path, line or course in both directions (as indicated by the bi-directional arrows associated with the longitudinal and lateral directions 500, 502). Likewise, the term "second direction" generally refers to a path, line or course rather than a vector (not orientation dependent), and includes for example and without limitation movement along a path, line or course in both directions. In one example, the first direction is defined by and refers to one of the longitudinal and lateral directions, while the second direction refers to the other of the longitudinal and lateral directions.

The term "body side" should not be interpreted to mean in contact with the body of the user, but rather simply means the side that would face toward the body of the user, regardless of whether an undergarment is actually being worn by the user and regardless of whether there are or may be intervening layers between the component and the body of the user. Likewise, the term "garment side" should not be interpreted to mean in contact with the garments of the user, but rather simply means the side that faces away from the body of the user, and therefore toward any outer garments that may be worn by the user, regardless of whether the undergarment is actually being worn by a user, regardless of whether any such outer garments are actually worn and regardless of whether there may be intervening layers between the component and any outer garment.

The phrases "removeably attached," "removeably attaching," "removeably connected," "removeably engaged," "releasably attached," "releasably connected," or "releasably engaged," and variations thereof, refers to two or more elements being connected or connectable such that the elements tend to remain connected absent a separation force applied to one, both or all of the elements, and where the elements are capable of being separated upon the application of a separation force. The required separation force is typically beyond that encountered while wearing the absorbent garment.

The phrases "fixedly secured," "fixedly engaged," "fixedly attached," "fixedly connected," and variations thereof, refers to two or more elements being connected or connectable such that they are not disconnected or otherwise separated, and are not intended to be separated or disconnected, during the normal operation and use of the absorbent garment.

The terms "connected," "coupled," "attached," and "secured," and variations thereof, broadly covers two or more items being directly connected one to the other, or by way of one or more intervening members or components.

As used herein, the interchangeable terms "stretchable" and "elastic," and variations thereof, refer to a material that can elongate or deform (stretch) in response to the application of a tensile force under certain test conditions herein defined below, and upon removal of the tensile force have a length that is less than about 128% of the original length, which corresponds to hysteresis of less than about 28%. Thus, a stretchable or elastic material can be stretched and upon relaxing the material, will tend to resume its original shape. As used herein, the term "extensible" refers to a material having a length of greater than about 128% of the original length when elongated and relaxed under certain test conditions herein defined below, which corresponds to a hysteresis of greater than about 28%.

The elasticity or extensibility of a material is quantified by a one-cycle tensile test without hold time. In this test, a 2 inch wide by 5 inch long specimen is cut from a sheet of sample material such that the stretchable/extensible direction of the material is in the length direction of the specimen, which is also the test direction. The sample is loaded onto a SYNERGIE 200 tensile tester (MTS, Eden Prairie, Minn.) by clamping the lengthwise ends of the sample in the jaws of the tester. The distance between the lower and upper jaws of the tensile tester are set at 3 inches, and the environmental conditions are maintained at 23° C. and 50% relative humidity during the loading of the sample and during the tensile test. The moving (upper) jaw is activated to travel at a constant rate of 5 inches/minute away from the stationary (lower) jaw. The moving jaw is stopped at an extension of 1.8 inches (60% extension). The moving jaw is then returned immediately to its initial starting position at a rate of 5 inches/minute. The load versus percentage strain for the tension and retraction cycle is recorded on a computer equipped with TestWorks Version 3.10 software program available from MTS. An elastic material will have a hysteresis strain of less than about 28%, or a length of less than about 128% of the original length. An extensible material will have a hysteresis strain of greater than about 28%, or a length of greater than about 128% of the original length.

In one example, shown in FIGS. 1–2, an undergarment 10 has a body chassis 12 that includes a front body panel 20 and a rear body panel 30. The terms "body chassis" and "body panel" refer to the portion(s) of the undergarment, whether made of one or more layers or substrates or of one or more pieces or components, that is/are fitted circumferentially around the body of the user, for example about the waist region of the user, and/or one or more of the user's lower back, buttock, hips, crotch and abdomen. Referring to FIG. 2, the front and rear body panels each have an inner, body side 21, 31 and an outer, garment side 22, 32. The front body panel 20 has a first terminal edge 23 formed at the buttocks region of the garment and a second terminal edge 24 formed along the waist region of the garment. The rear body panel 30 has a first terminal edge 33 formed near the buttocks region of the garment and a second terminal edge 34 that is formed along the waist region of the garment. In one example, the first and second terminal edges of the front and rear body panels are linear. In another example, the first and second terminal edges of the front and rear body panels are curvilinear, such as sinusoidal.

The front body panel has a front side edge 25 and a rear side edge 26 formed along the outer periphery of the opposite side portions of the front body panel. The front and rear side edges 25, 26 may be the same length, or they could have different lengths relative to each other. The middle side edge 27 connects the front and rear side edges and defines a portion of a leg opening 14. The middle side edge 27 may include one or more discreet linear portions, and it may include one or more nonlinear portions. For example, the entire middle side edge may be curvilinear. In another example, as illustrated in FIG. 1, the middle side edge 27 includes tapered portions 29 and 39 and longitudinal portion 28.

The rear body panel has a side edge 35 formed along the outer periphery of the opposite side portion of the rear body panel. In one example, the side edge 35 is the same length as the front side edge 25 of the front body panel, although it should be understood that the side edge of the rear body panel and the front side edge of the front body panel could have different lengths relative to each other. In one example, a tapered edge 37 connects the terminal edge 33 with the side edge 35 and defines a portion of leg opening 14. In one example, the terminal edges 33, 34 are linear and extend across the entire lateral width of the garment without any tapered edges.

In another example, shown in FIGS. 3–4, the undergarment 100 has a body chassis 112 that includes a front body panel 120 and a rear body panel 130. Referring to FIG. 4, the front and rear body panels each have an inner, body side 121, 131 and an outer, garment side 122, 132. The front body panel 120 has a first terminal edge 123 formed along the crotch region of the garment and a second terminal edge 124 formed along the waist region of the garment. The rear body panel 130 has a first terminal edge 133 formed near the crotch region of the garment and a second terminal edge 134 that is formed along the waist region of the garment. The terminal edges 123, 133 of the front and rear body panels are spaced apart in the crotch region so as to form a gap or space 116 therebetween. In one example, the first and second terminal edges of the front and rear body panels are linear but can assume other shapes.

Each of the front and rear body panels have a side edge 125, 135 formed along the outer periphery of the opposite side portions of the front and rear body panels. In one example, the side edges 125, 135 may be the same length, although it should be understood that the side edges of the front and rear body panels could have different lengths relative to each other. In one example, tapered edges 127, 137 connect the terminal edges 123, 133 with the side edges 125, 135, respectively, and define a portion of leg opening 114. In one example, the terminal edges 123, 124, 133, 134 are linear and extend across the entire lateral width of the garment without any tapered edges.

One or more separate leg flaps 40, 140 can be secured to one or both of the rear and front body panels along the edges forming and defining the leg openings 14, 114. Referring to the example of FIG. 1, the leg flaps can be secured to one or both of the tapered portions 29, 39, to the longitudinal portion 28 and/or to the tapered edge 37. Referring to the example of FIG. 3, the leg flaps can be secured to one or both of the tapered edges 127 and 137 and can also span the crotch gap 116. In either arrangement, the leg flaps may be secured to the absorbent composite 50, 150.

In one example, a plurality of elastic elements can be secured to the front body panel (20, 120) and/or to the rear body panel (30, 130). In one example, a plurality of elastic elements are spaced across substantially the entire waist portion of the front and rear body panel, although they may be spaced across a lesser length. For example, elastic elements can extend along the upper waist portion and along the lower terminal edge defining in part a leg opening. In another example, one or more elastic elements can be secured along the elements forming the leg openings 14, 114. These elastic elements may be secured to the front and/or rear body panels, to the leg flaps, and/or to the absorbent composite 50, 150.

In one embodiment, the front body panel has a "non-elasticized" area wherein there are no elastic elements, or other elastic or elastomeric backing members, incorporated therein or making up any portion of the thickness or cross-section of the body panel at that area. It should be understood, that in various aspects, one or more separate waist bands, with or without elastic elements, can be secured to one or both of the rear and front body panels, preferably along the second terminal edges 24, 34, 124, 134 thereof. In another example, one or both of the body panels can be formed without any elastic elements.

The various waist and leg elastic elements can be formed from rubber or other elastomeric materials. One suitable material is a LYCRA® elastic material. For example, the various elastic elements can be formed of LYCRA® XA Spandex 540, 740 or 940 decitex T-127 or T-128 elastics available from E.I. duPont De Nemours and Company, having an office in Wilmington, Del.

The body chassis 12, 112, including front and rear body panels 20, 30, 120, 130 independently, can be made of a single layer or substrate of non-woven material, a bi-layer substrate made of non-woven materials without an elastic core, or more than two layers or substrates. Of course, it should be understood that other knitted or woven fabrics, non-woven fabrics, elastomeric materials, polymer films, laminates and the like can be used to form one or more of the body panel layers. The term "non-woven" web or material, as used herein, means a web having a structure of individual fibers or filaments that are interlaid, but not in an identifiable manner and without the aid of textile weaving or knitting, as in a knitted or woven fabric. In various examples, the body panel material may be substantially permeable to air or substantially impermeable to air. The body chassis material also may be substantially liquid-permeable or substantially liquid-impermeable. In particular arrangements, the body chassis material may be substantially non-elastomeric. For a given undergarment, the front and rear body panels may be the same material, or they may be different materials.

The body chassis non-woven material is preferably substantially hydrophobic, which may optionally be treated with a surfactant or otherwise processed to impart a desired level of wettability and hydrophilicity. In one particular example, a body panel is a nonwoven, wire-weave spunbond polypropylene fabric composed of about 1.6 denier fibers formed into a web having a basis weight of about 0.6 osy. One suitable non-woven material is the Corinth 0.60 osy, 1.6 dpf wireweave, nonwettable Metallocene (EXXON ACHIEVE 2854 PP) spunbond material manufactured by Kimberly-Clark Corporation, the assignee of the present application.

The front body panel or the rear body panel material may be extensible but not elasticized. For example, a body panel can be made of a film or non-woven that is attached, by way of adhesives or thermal bonding, to an extensible non-woven material. In another example, the body panel can be made of a low modulus film such as Ethylene Methyl acrylate (EMA). In another example, the body panel is a breathable, cloth-like, multi-directional nonwoven laminate with extensible properties. In another example, the non-woven layers are pre-necked, for example between about 10% and about 80%, in the longitudinal direction, which provides extensibility in the longitudinal direction with minimal force. As used herein, the term "necked," and variations thereof, refers to any material that has been constricted in at least one dimension by applying a tensioning force in a direction that is perpendicular to the desired direction of neck-down. Processes that may be used to constrict a material in such a manner include, for example and without limitation, drawing processes.

Preferably, at least one of the front body panel and the rear body panel preferably is an elastic material. In one example, a body panel is a unitary sheet of an elastomeric film or nonwoven elastic or stretchable material, including for example block copolymers of polystyrene, polyisoprene or polybutadiene, copolymers of ethylene, natural rubbers, urethanes, kratons, and co-extrusions/blends of the aforementioned material. In another example, referring to FIG. 5, the body panel 90 may be formed as a composite, or laminate material, otherwise referred to as substrates or laminates, with an elastic core 80 sandwiched therebetween. The elastic core 80 may be a unitary sheet of an elastomeric film or nowoven elastic or stretchable material. The elastic core can be formed as a membrane or from a plurality of elastic strands, as described above. Two or more outer layers 82, 84 may be bonded to the elastic core 80 and/or each other, with various adhesives, such as hot melt, or by other techniques, including for example and without limitation ultrasonic bonding and heat pressure sealing. In one example, the two outer layers are made of a non-woven material such as a spunbond material, a bonded carded material or other known materials. In this way, the body panel is made of a stretchable/elastic material.

In one example, the outer layer material 82, 84 can be secured to the elastic core, such as an elastomeric layer or elastic strands or ribbons, which have been elongated and retracted, such that the material is gathered when the elastic element(s) are relaxed. Alternatively, the material can be gathered and laminated to non-elongated elastic elements. In one preferred embodiment, the body panel includes a gathered elastic laminate made from nonwoven base sheets bonded with elongated elastic elements sandwiched therebetween.

Examples of elastomeric composite materials include continuous filament stretch bonded laminates (CFSBL), vertical filament laminates (VFL), neck-bonded-laminates (NBL), stretch-bonded-laminates (SBL), necked-stretch bonded laminates (NSBL) or necked-thermal laminates, or the like, as well as combinations thereof. Exemplary CFSBL, NBL, SBL, and NSBL materials are described in U.S. Pat. Nos. 5,226,992, 4,981,747, 4,965,122, 5,336,545, 5,385,775, 5,414,470, 4,720,415, 4,789,699, 4,781,966, 4,657,802, 4,652,487, 4,655,760, 5,116,662 and 5,114,781, and 6,323,389, all of which are hereby incorporated herein by reference. Exemplary VFL materials are described in U.S. patent application Ser. No. 09/855,169, filed May 14, 2001, entitled "Method and Apparatus for Producing Laminated Articles," published as US 2002/0104608, and assigned to Kimberly-Clark Worldwide, Inc., the Assignee of the present application, with the entire disclosure being hereby incorporated herein by reference. Such laminates can provide an improved combination of cloth-like feel and elastomeric stretchability. The front and rear body panels can be composed of materials that are elastic or elastomeric and exhibit biaxial stretch characteristics or lateral/longitudinal stretch characteristics, or which are extensible composites. Additional waist and leg elastic elements can be added to, but are not necessarily required by, the body panels.

In one example, a body panel 20, 30, 120, 130 is made of a non-woven laminate of two layers of longitudinally extensible 0.60 osy polypropylene spunbond material with elongated strands of Lycra® elastic sandwiched between the spunbond layers and thereafter adhesively bonded. In particular, the body panel material is necked in the cross direction. The elastics are then elongated in the machine direction and secured to the body panel material. The elastics are then allowed to retract so as to gather the necked spunbond material in the lateral (machine) direction thereby creating an elastically gathered non-woven body panel with longitudinal extensibility. The term "gather," and variations thereof, as used herein means puckered, or contracted into folds or wrinkles, which should be understood as including micro-pleats.

Preferably, the entirety of the rear body panel 30, 130 is elasticized, such that the entirety of the rear body panel can elongate and conform to the body of the user without any substantial spacing between the body panel and the user's body, and without the attendant bulkiness of a non-elasticized material. In this way, the body panel can be elongated in both the longitudinal and lateral direction to conform to the body of the user when the garment is applied thereto. In particular, as the user pulls the garment up over their hips, the elastic rear body panel stretches in the lateral direction while the leg regions of the garment conform to the crotch and body lines of the user. At the same time, the rear body panel material extends in the longitudinal direction to conform to the buttocks of the user. The stretchability of the body panel follows the natural curvature of user's body to provide conformance thereto. In this example, it is preferred that the front body panel is extensible; however, it is to be understood that the front body panel can also be stretchable. The tendency of the elastic rear body panel to retract after it has been stretched can impose an elongation force on the front body panel when the garment is applied to the body of the user. The elongation force causes the extensible front body panel to conform more closely to the natural curvature of the user's body, further aiding in the reduction of bulkiness.

In another example, the entirety of the front body panel 20, 120 is elasticized, such that the entirety of the front body panel can elongate and conform to the body of the user without any substantial spacing between the body panel and the user's body, and without the attendant bulkiness of a non-elasticized material. As described above for an elastic rear body panel, as the user pulls the garment up over their hips, the elastic front body panel stretches in the lateral direction while the leg regions of the garment conform to the crotch and body lines of the user, and the front body panel material extends in the longitudinal direction to conform to the front of the user. In this example, it is preferred that the rear body panel is extensible; however, it is to be understood that the rear body panel can also be stretchable. The combination of an elastic front body panel and an extensible rear body panel likewise can increase the conformity of the entire garment to the user's body.

Referring to FIGS. 1–4, the absorbent garment includes an absorbent composite 50, 150 having a front terminal edge 53, 153 near the front of the garment and a rear terminal edge 54, 154 near the rear of the garment. Referring to the cross-section views of FIGS. 2–4 and 6–9, the absorbent composite has an inner, body side 51, 151 and an outer, garment side 52, 152. The absorbent composite preferably includes a substantially liquid permeable topsheet 55, 155, or liner, and a substantially liquid impermeable backsheet 56, 156, or outer cover. A retention portion 57, 157 is disposed or sandwiched between the topsheet and the backsheet, which are connected.

The topsheet, backsheet and other components of the absorbent composite 50, 150 can be joined for example with adhesive bonds, sonic bonds, thermal bonds, pinning, stitching or any other attachment techniques known in the art, as well as combinations thereof. For example, a uniform continuous layer of adhesive, a patterned layer of adhesive, a sprayed pattern of adhesive or any array of lines, swirls or spots of construction bonds may be used to join the topsheet and backsheet, or any of the other components described herein. It should be understood that the term "absorbent composite" refers to any material or assembly capable of absorbing liquids or bodily exudates, and may be comprised of a single material or component, for example a retention portion.

Additional layers, including for example, a surge layer 58, 158, are also preferably incorporated into the absorbent composite. Preferably, the surge layer does not run the entire length of the absorbent composite and is shorter than the retention portion. The topsheet can be indirectly joined to the backsheet by affixing the topsheet to intermediate layers, such as the surge layer or retention portion, which in turn is affixed to the backsheet. The absorbent composite can further include one or more longitudinally extending barrier cuffs formed along the opposite lateral sides of the absorbent composite on the body side surface thereof. These cuffs may be present in addition to or in place of the leg flaps 40, 140.

In various constructions, the topsheet 55, 155 can comprise various woven or nonwoven materials. For example, the topsheet can be composed of a meltblown or spunbonded web of desired fibers, and may also be a bonded-carded web. For example, the topsheet can be made of a substantially hydrophobic material, and the hydrophobic material may optionally be treated with a surfactant or otherwise processed to import a desired level of wettability and hydrophilicity. In one particular embodiment of the invention, the topsheet is a nonwoven, spunbond polypropylene fabric composed of about 2.8–3.2 denier fibers formed into a web having a basis weight of about 22 gsm and density of about 0.06 gm/cc. The fabric can be surface treated with an operative amount of surfactant, such as about 0.28% Triton X-102 surfactant. The surfactant can be applied by any conventional means, such as spraying, printing, brush coating or the like.

The backsheet 56, 156 is preferably fluid impermeable, but may be fluid permeable, e.g., when an additional barrier layer is used with the retention portion. For example, in one embodiment, the backsheet can be made from a thin plastic film, or other flexible, substantially liquid-impermeable material. As used herein, the term "flexible" means a material that is compliant and which will readily conform to the general shape and contour of the body of the user. The backsheet prevents various bodily fluids and exudates from wetting or otherwise contaminating various bedding or outer garments worn by the user over the absorbent garment. In particular, the backsheet can include a film, such as a polyethylene film, having a thickness of from about 0.012 mm to about 0.051 mm.

In various constructions, the backsheet 56, 156 can comprise a woven or nonwoven fibrous web layer, which is treated or constructed, partially or wholly, to impart the desired levels of liquid impermeability to selected regions that are adjacent to or proximate the absorbent retention portion. For example, the backsheet may include a gas-permeable, nonwoven fabric layer laminated to a polymer film layer which may or may not be gas-permeable. Other examples of fibrous, cloth-like backsheet materials can comprise a stretch thinned or stretch thermal laminate material composed of a 0.6 mil (0.015 mm) thick polypropylene cast film and a 0.7 ounce per square yard (23.8 gsm) polypropylene spunbond material (2 denier fibers). A material of this type has been employed to form the outercover of a HUGGIES® Ultratrim Disposable Diaper, which has been commercially available from Kimberly-Clark Corporation. The backsheet can provide the outercover of the article, particularly in the crotch region. Optionally, however, the article may include a separate outercover component member, as disclosed herein, which is additional to the backsheet. The outercover can be joined, for example, to one or more of the absorbent composite and/or body panels as explained above.

The backsheet may include a micro-porous, "breathable" material that permits gases, such as water vapor, to escape from the absorbent garment while substantially preventing liquid exudates from passing through the backsheet. For example, the breathable backsheet may be composed of a microporous polymer film or a nonwoven fabric that has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In various configurations of the invention, where a component, such as the backsheet is configured to be permeable to gas while having a resistance and limited permeability to aqueous liquid, the liquid resistant component can have a construction that is capable of supporting a selected hydrohead of water substantially without leakage therethrough. A suitable technique for determining the resistance of a material to liquid penetration is Federal Test Method Standard FTMS 191 Method 5514, 1978, or an equivalent thereof.

In one preferred embodiment, the backsheet is sufficiently impermeable to liquid and semi-liquid materials to substantially prevent the undesired leakage of waste materials, defined as exudates, including for example urine and feces. For example, the backsheet member can desirably support a hydrohead of at least about 45 centimeters (cm) substantially without leakage. The backsheet member can alternatively support a hydrohead of at least about 55 cm, and optionally, can support a hydrohead of at least about 60 cm, or more, to provide improved benefits.

The backsheet and/or outercover also can be extensible. In one preferred embodiment, the backsheet and/or outercover is capable of providing an elongation of at least about 1 cm when subjected to a tensile force of 11.8 g/cm, and further provides a substantially permanent deformation of at least about 20% when subjected to a tensile force of 19.70 g/cm and is then allowed to relax under a zero applied stress for a period of 1 minute. For example, the extensible member can be composed of a necked fiber, a creped fiber, a micro-pleated fiber, polymer films or the like, as well as combinations thereof. The fabrics may be woven or nonwoven materials, such as spunbond fabrics. One example of a suitable extensible material is a 60% necked, polypropylene spunbond having a basis weight of about 1.2 osy. The backsheet and/or outercover also can be expandable, for example when it has one or more folds, e.g., one or more z-folds (not shown), or can be both extensible and expandable. The term expandable as used herein means to enlarge or to increase the extent or area, lateral and/or longitudinal, thereof, e.g., by unfolding one or more folds.

The retention portion 57, 157 is preferably made of an absorbent material, which can be any material that tends to swell or expand as it absorbs exudates, including various liquids and/or fluids excreted or exuded by the user. For example, the absorbent material can be made of airformed, airlaid and/or wetlaid composites of fibers and high absorbency materials, referred to as superabsorbents. Superabsorbents typically are made of polyacrylic acids, such as FAVOR 880 available from Stockhausen, Inc. of Greensboro, N.C. The fibers can be fluff pulp materials, such as Alliance CR-1654, or any combination of crosslinked pulps, hardwood, softwood, and synthetic fibers. Airlaid and wetlaid structures typically include binding agents, which are used to stabilize the structure. In addition, various foams, absorbent films, and superabsorbent fabrics can be used as an absorbent material. Various acceptable absorbent materials are disclosed in U.S. Pat. No. 5,147,343 to Kellenberger for Absorbent Products Containing Hydrogels With Ability To Swell Against Pressure, U.S. Pat. No. 5,601,542 to Melius et al. for Absorbent Composite, and U.S. Pat. No. 5,651,862 to Anderson et al. for Wet Formed Absorbent Composite, all of which are hereby incorporated herein by reference. Furthermore, the proportion of high-absorbency particles can range from about 0 to about 100%, and the proportion of fibrous material from about 0 to about 100%. Additionally, high absorbency fibers can be used such as Oasis type 121 and type 122 superabsorbent fibers available from Technical Absorbent Ltd., Grimsby, Lincolnshire, United Kingdom.

The retention portion 57, 157 can be made of a single or dual layer of absorbent material. The retention portion preferably has an hour-glass shape with enlarged end regions. Alternatively, the retention portion can include a folded or multi-layered configuration. The retention portion preferably has a length substantially equal to, or slightly shorter than, the length of the absorbent composite. The retention portion can include one or more barrier layers attached to the absorbent material. In one embodiment, an upper tissue substrate is disposed adjacent the retention portion. Alternatively, a lower tissue substrate can be disposed adjacent an opposite side of the retention portion, or the tissue can completely envelop the retention position.

Referring to FIGS. 1–4 and 7–8, the garment side of at least the front terminal edge 53, 153 is connected to the body side of the of the front body panel 20, 120. In one example, referring to FIGS. 1–2 and 7, the garment side of backsheet 56 is secured along its length to the body side of front body panel 20. In this example, the attachment between the absorbent composite and the front body panel can extend along the entire length of the absorbent composite, along only a portion of the length, or at a discrete point, for example proximate midway between the terminal edges 53, 54 of the absorbent composite. The attachment location also can be formed from a plurality of discrete attachment locations spaced longitudinally along the entire length of the absorbent composite. The entire absorbent composite can be attached to the front body panel with a continuous attachment across the width of the absorbent composite, or across a portion of the width.

Figure 8:
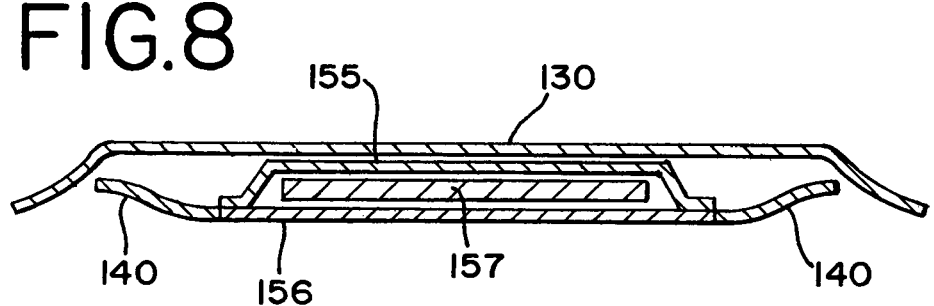
FIG. 8 is a schematic illustration of a cross-sectional view of the disposable undergarment taken along line 8—8 in FIG. 3.
Figure 9:
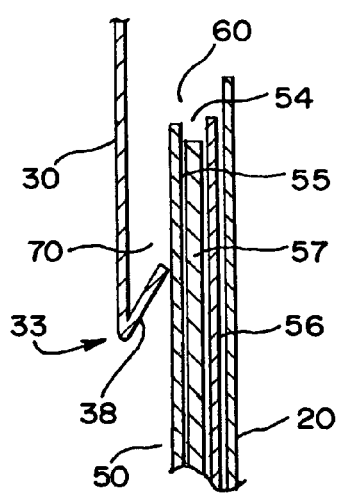
FIG. 9 is a schematic illustration of an exemplary modification to the disposable undergarment of FIG. 2.

In another example, referring to FIGS. 3–4 and 8, the garment side of the backsheet and/or outercover is secured at one or more points to the body side of front body panel 120. In this example, the backsheet and/or outercover is not secured on the garment side to any other element. It should be understood that the absorbent composite can be connected to the front body panel using any of the methods of attachment described above, including for example various adhesives, stitching or other bonding methods. The absorbent composite can be secured to the front body panel with any configuration of attachment lines, swirls, patterns, spots, etc., or can be a full and continuous attachment therebetween.

Referring to FIGS. 1–4, the body side of the rear terminal edge 54, 154 is connected to the garment side of the of the rear body panel 30, 130. In one example, referring to FIGS. 1–2, the absorbent composite 50 can be connected to the garment side of the rear body panel 30 by way of the attachment between the front and rear body panels. The body side of the front body panel overlaps the garment side of the rear body panel by the distance between terminal edge 23 and terminal edge 33, forming a body panel overlap region 60. Preferably the front and rear body panels are secured along the terminal edge 23 and the rear side edges 26, forming a partial periphery to the panel overlap region 60. The absorbent composite likewise overlaps the rear body panel by the distance between the rear terminal edge 54 and the terminal edge 33, forming an absorbent overlap region 70.

In another example, referring to FIGS. 3–4, the body side of topsheet 155 is connected to the garment side of rear body panel 130 along the rear terminal edge 154. The absorbent composite overlaps the rear body panel by the distance between the terminal edge 154 and the terminal edge 133, forming an absorbent overlap region 170. The absorbent composite may be secured only along the terminal edge 154, or along the terminal edge and the overlapped portions of the side edges 159 of the composite. Preferably the rear body panel and the absorbent composite are secured both along the terminal edge and the overlapped portions of the side edges 159, forming a partial periphery to the absorbent overlap region 170. It should be understood that the absorbent composite 50 in the configuration of FIG. 1 can be connected to the rear body panel 30 in a similar way, and that this connection may be present place of or in addition to the connection between the front and rear body panels.

In the examples illustrated in FIGS. 1–4, a pocket can be formed in the overlap region between the rear body panel 30, 130 and the absorbent composite 50, 150. The boundaries of the pocket are defined by the connections along the terminal edge 23, 154 and along the side edges 26, 159. The opening of the pocket is defined by the length of the front terminal edge 33, 133 of the rear body panel that is not secured to any other elements of the undergarment. Referring to FIG. 1, the terminal edge 33 preferably is not connected to the front body panel or to the absorbent composite. Referring to FIG. 3, the terminal edge 133 preferably is not connected to the absorbent composite. It should be understood that a portion of the terminal edge 33, 133 can be connected to the absorbent composite and/or front body panel and can still create a pocket. For example, the garment side of rear body panel 30 can be connected to the body side of front body panel 20 along the portions of terminal edge 33 that extend between the absorbent composite and the tapered edge 37. Although the illustrated pockets have a generally rectilinear "U" shape, other configurations which define a pocket and an opening may be used. In general, such pockets may be described as including a substantially continuous seam that terminates at two separate points, such that a line drawn between the two points, together with the seam, defines a closed figure having an area.

The opening of the pocket is advantageously positioned on the undergarment 10, 110 such that it is located above the anus of the wearer when the undergarment is in use. It is also advantageous to position the opening of the pocket on the undergarment so that it will be located above the gluteal groove of the wearer when the undergarment is in use. Positioning the pocket opening above the gluteal groove of the wearer allows the pocket formed by the rear body panel together with the absorbent composite and/or the front body panel to be well-positioned to receive and contain fecal materials expelled by the wearer, such as those materials which travel upwards along the gluteal groove. In small infants and the elderly in particular, low viscosity fecal materials may be forced along the gluteal groove of the wearer. The pocket opening is not limited to such positions, however, and may be positioned at a variety of locations by changing the distance between the first terminal edge 33, 133 and the second terminal edge 34, 134. Containing fecal materials in the pocket limits the amount of contact between the fecal materials and the skin of the wearer while the article is being worn. Limiting the amount of contact with fecal materials can provide skin health benefits to the wearer. Containing fecal materials in the pocket also reduces the chances of contact between the fecal materials and the skin and clothing of either the wearer or the caregiver during the removal process.

Figure 10:
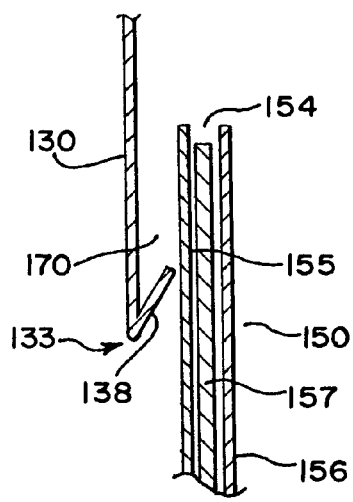
FIG. 10 is a schematic illustration of an exemplary modification to the disposable undergarment of FIG. 4.

The containment of fecal materials, especially low viscosity fecal materials, can be further promoted by incorporating additional containment structures in the overlap region. Additional containment structures can prevent bodily exudates from migrating out of the pocket during use due to gravity. For example, a physical barrier can be incorporated into the pocket, so as to block the flow of fecal materials from migrating after the materials have entered the pocket. For example, referring to FIGS. 9–10 the rear body panel 30, 130 can contain additional material 38, 138 that is folded back past the terminal edge 33, 133 and into the overlap region 60, 70, 170. This additional material can function as a barrier flap to impede the flow of fecal materials from the overlap region. The barrier flap 38, 138 may be an extension of the rear body panel material, or it may be a different material. It may be desirable for the barrier flap to have a greater thickness than the rear body panel. It may also be desirable for the barrier flap 38, 138 to be a hydrophobic material, and the barrier flap may be treated with a surfactant or other hydrophobic treatment.

Figure 11:
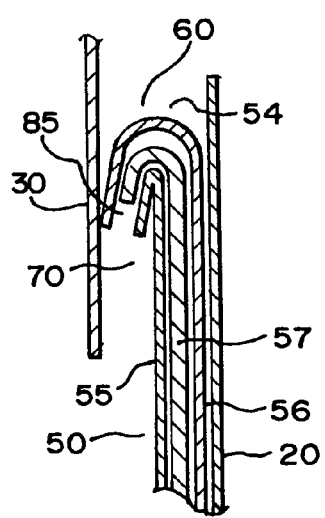
FIG. 11 is a schematic illustration of an exemplary modification to the disposable undergarment of FIG. 2.
Figure 12:
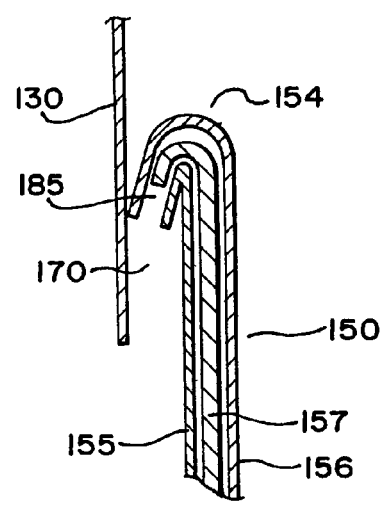
FIG. 12 is a schematic illustration of an exemplary modification to the disposable undergarment of FIG. 4.

In another example, additional absorbent material can be incorporated into the pocket, so as to reduce the amount of fluid material. For example, referring to FIGS. 11–12 the absorbent composite 50, 150 can contain additional absorbent material 85, 185 that is folded back past the rear terminal edge 54, 154 and into the overlap region 60, 70, 170. This additional absorbent material can help to retain fecal material in the overlap region. The additional absorbent material 85, 185 may be an extension of the absorbent composite material, or it may be a different material, such as a fibrous material without any superabsorbent. For example, fibrous materials can provide void spaces that serve to entrap small fecal particulates. Enhanced absorbent capacity and the ability to entrap fecal particulates are particularly advantageous for use with fecal materials having a high fluid content, such as those often produced by small infants. It should be understood that a barrier flap 38, 138 may be present in addition to the additional absorbent material 85, 185. In other examples, the additional absorbent material may be connected to the barrier flap instead of, or in addition to, being connected to the absorbent composite.

For undergarments intended for use as a pant-like garment, the absorbent composite 50, 150 can be folded to bring the body sides of the front and rear body panels into closer proximity. In this way, the side edges 25, 125 of the front body panel are aligned with the side edges of the rear body panel 35, 135, whereinafter they can be fixedly secured at a seam to form the leg opening 14, 114. The seam can be formed by bonding, sewing or otherwise attaching the side edges. For undergarments intended for use as a diaper-like garment, the product can remain "open," wherein the body panels are releasably secured with one or more fastening members as explained below.

In one example, the garment includes a combination of side edges that are secured to form a seam and fastening members that allow the fit of the undergarment to be adjusted. For example, the fastening members are preferably attached to the front body panel and extend inboard relative to the outboard side edge of the front body panel from an attachment location, which is preferably spaced inboard from the side edge. A landing member can be formed on or secured to the body panel to receive a refastenable portion of the fastening member. One or more lines of weakness can be provided along the front or rear body panel such that one or both of the body panels are breakable. The lines of weakness can comprise a perforation or other series of cuts, a thinning, breakage or separation of material, or a strip of a different kind of material bridging portions of the body panel that is more easily torn or broken than the other material thereof, which allow a user or the manufacturer to separate portions of the body panel. For example, the undergarment can be broken along the lines of weakness after the garment is applied to a user, or beforehand. In one embodiment, the fastening members are secured to the garment side of the body panel.

It should be understood that the fastening members can be secured to the rear body panel and engage the front body panel or, conversely, can be secured to the front body panel and engage the rear body panel, preferably along at least a portion that is not elasticized. In one example, the fastening members are fixedly secured to the outer, garment side of the front and/or rear body panels, and releasably engage the outer, garment side of the front and/or rear body panels, although it should be understood that the fastening members could be fixedly secured to an inner body side of front and/or rear body panels and releasably engage an inner, body side of the front and/or rear body panels.

When incorporated into a disposable absorbent undergarment, the fastening members can include a refastenable portion, such as an array of hook members, adhesives, such as pressure sensitive adhesives, buttons, zippers, snaps and other releasable and reattachable fastening devices. In various examples, the fastening member includes one, two or more than two tab members. In one example, the fastening members comprise a carrier member, which is preferably fixedly secured to the side portions of the front body panel with adhesive bonds, sonic bonds, thermal bonds, pinning, stitching or other known types of attachment. In other examples, the fastening members can be fixedly secured to the rear body panel or to one or both of the front and rear body panels, for example, at the seam, as explained above.

In operation, the user applies the undergarment to a body, whether by way of pulling it up around the waist as a pant-like garment or by way of fastening it about the waist with fasteners as a diaper-like garment. The body may be the body of the user, or it may be the body of another person, such as an infant, a child or an adult. As the garment is applied or fitted to the body, the body chassis 12, 112, and especially the rear body panel 30, 130, are elongated from a first condition, preferably relaxed, to a second condition, preferably elongated, in at least one direction, preferably the lateral direction 502. Of course, the body chassis 12, 112 can also elongate in the longitudinal direction 500 from the crotch to the waist. In one embodiment, the body chassis 12, 112, and in particular the rear body panel 30, 130, is elongated in a lateral direction between about 20% and about 300%, in another embodiment between about 50% and about 200%, and in another embodiment between about 100% and about 150%, as it is applied to the user. The body chassis 12, 112 is elongated by virtue of a tensile force being applied thereto as the body chassis conforms to the body.

In another aspect, the manufacturer or retailer of the absorbent garments provides instructional information to the user, for example by way of textual or pictorial indicia on the packaging materials, about how the garment works. For example, the manufacturer or retailer can explain to the end user the advantages of the elastic body panel or panels and/or the containment pocket formed by the rear body panel and the absorbent composite, and the resultant ability of the body panels to freely conform to the body of the user without restriction from the retention portion, thereby improving the conformance and fit of the garment.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

The invention claimed is:

1. A disposable undergarment, comprising:
   a front body panel comprising a body side, a garment side, a terminal waist edge and a terminal rear edge, wherein the front body panel is stretchable and comprises an elastic material;
   a rear body panel comprising a body side, a garment side, a terminal waist edge and a terminal front edge, wherein the rear body panel is stretchable and comprises an elastic material;
   wherein the terminal rear edge of the front body panel is longitudinally spaced from and forms a gap with the terminal front edge of the rear body panel; and
   an absorbent composite bridging the gap and comprising a front terminal edge and a rear terminal edge;
   wherein the absorbent composite overlaps the terminal front edge of the rear body panel and is connected to the garment side of the rear body panel to form an overlap region; and
   wherein the absorbent composite overlaps the terminal rear edge of the front body panel and is connected to the body side of the front body panel.

2. The disposable undergarment of claim 1, wherein the elastic material comprises an elastic film.

3. The disposable undergarment of claim 1, wherein the front body panel is extensible.

4. The disposable undergarment of claim 1, wherein the rear body panel is extensible.

5. The disposable undergarment of claim 1, wherein the terminal rear edge of the front body panel is longitudinally spaced from the terminal waist edge of the rear body panel.

6. The disposable undergarment of claim 1, wherein at least a portion of the terminal front edge of the rear body panel is not connected to the absorbent composite.

7. The disposable undergarment of claim 1, wherein at least a portion of the overlap region comprises a pocket containing a pocket opening positioned on the undergarment to receive or contain fecal materials from the wearer when the undergarment is in use.

8. The disposable undergarment of claim 1, wherein the overlap region further comprises a containment structure configured to prevent bodily exudates from migrating out of the pocket during use of the disposable undergarment.

9. The disposable undergarment of claim 8, wherein the containment structure is a barrier flap extending from the terminal front edge of the rear body panel into the overlap region.

10. The disposable undergarment of claim 8, wherein the containment structure includes an additional material from the absorbent composite folded back past the rear terminal edge of the absorbent composite.

11. The disposable undergarment of claim 10, wherein the additional material comprises absorbent material.

12. A method of using a disposable undergarment, comprising:
   providing a disposable undergarment comprising:
   a front body panel comprising a body side, a garment side, a terminal waist edge and a terminal rear edge;
   a rear body panel comprising a body side, a garment side, a terminal waist edge and a terminal front edge; and
   an absorbent composite comprising a front terminal edge and a rear terminal edge;

wherein each of the front and rear body panels is stretchable and comprises a first elastic material; and wherein the terminal rear edge of the front body panel is longitudinally spaced from and forms a gap with the terminal front edge of the rear body panel;

wherein the absorbent composite bridges the gap;

wherein the absorbent composite overlaps the terminal front edge of the rear body panel and is connected to the garment side of the rear body panel to form an overlap region; and wherein the absorbent composite overlaps the terminal rear edge of the front body panel and is connected to the body side of the front body panel; and stretching at least one of the front body panel and the rear body panel.

13. A method of instructing a user in the use of a disposable undergarment, comprising:

providing a disposable undergarment comprising:

a front body panel comprising a body side, a garment side, a terminal waist edge and a terminal rear edge;

a rear body panel comprising a body side, a garment side, a terminal waist edge and a terminal front edge; and an absorbent composite comprising a front terminal edge and a rear terminal edge;

wherein each of the front and rear body panels is stretchable and comprises a first elastic material; and wherein the terminal rear edge of the front body panel is longitudinally spaced from and forms a gap with the terminal front edge of the rear body panel;

wherein the absorbent composite bridges the gap;

wherein the absorbent composite overlaps the terminal front edge of the rear body panel and is connected to the garment side of the rear body panel to form an overlap region; and wherein the absorbent composite overlaps the terminal rear edge of the front body panel and is connected to the body side of the front body panel; and instructing the user to apply the undergarment to a body; and advising the user that the application of the undergarment to the body will stretch at least one of the front body panel and the rear body panel in at least one direction.

14. A disposable undergarment comprising:

a front body panel comprising a body side, a garment side, a terminal waist edge and a terminal rear edge;

a rear body panel comprising a body side, a garment side, a terminal waist edge and a terminal front edge; and an absorbent composite comprising a front terminal edge and a rear terminal edge, wherein the absorbent composite overlaps with and is connected to the garment side of the rear body panel to form an overlap region, and wherein the absorbent composite overlaps with and is connected to the body side of the front body panel;

wherein at least a portion of the terminal front edge of the rear body panel is not connected to the absorbent composite and wherein at least a portion of the overlap region comprises a pocket with a pocket opening positioned between the terminal front edge of the rear body panel and the absorbent composite.

15. The disposable undergarment of claim 14, wherein each of the rear body panel and the front body panel is stretchable and comprises an elastic material.

16. The disposable undergarment of claim 14, wherein the entirety of at least one of the front body panel or the rear body panel is elasticized.

17. The disposable undergarment of claim 14, wherein either of the front body panel or the rear body panel is extensible.

18. The disposable undergarment of claim 16, wherein the overlap region further comprises a containment structure configured to prevent bodily exudates from migrating out of the pocket during use of the disposable undergarment.

19. The disposable undergarment of claim 18, wherein the containment structure is a barrier flap extending from the terminal front edge of the rear body panel into the overlap region.

20. The disposable undergarment of claim 18, wherein the containment structure includes an additional material from the absorbent composite folded back past the rear terminal edge of the absorbent composite.

21. The disposable undergarment of claim 20, wherein the additional material comprises absorbent material.

22. A disposable undergarment comprising:

a front body panel comprising a body side, a garment side, a terminal waist edge and a terminal rear edge;

a rear body panel comprising a body side, a garment side, a terminal waist edge and a terminal front edge;

an absorbent composite comprising a front terminal edge and a rear terminal edge, wherein the absorbent composite overlaps the terminal front edge of the rear body panel and is connected to the garment side of the rear body panel to form an overlap region, and wherein the absorbent composite overlaps the front body panel and is connected to the body side of the front body panel;

wherein the terminal rear edge of the front body panel is longitudinally spaced from the terminal waist edge of the rear body panel;

wherein the terminal front edge of the rear body panel is longitudinally spaced from the terminal rear edge of the front body panel; and wherein each of the rear body panel and the front body panel is stretchable and comprises an elastic material.

23. The disposable undergarment of claim 22, wherein the terminal rear edge of the front body panel forms a longitudinal gap with the terminal front edge of the rear body panel, such that the absorbent composite bridges the gap between the front and rear body panels.

24. The disposable undergarment of claim 22, wherein the terminal rear edge of the front body panel overlaps the terminal front edge of the rear body panel.

25. The disposable undergarment of claim 22, wherein at least a portion of the overlap region comprises a pocket having a pocket opening.

* * * * *